(12) United States Patent
Gibbons, Jr. et al.

(10) Patent No.: US 7,465,754 B1
(45) Date of Patent: *Dec. 16, 2008

(54) METHOD OF POTENTIATING CHEMOTHERAPY AND TREATING SOLID TUMORS

(75) Inventors: James J. Gibbons, Jr., Westwood, NJ (US); Gary Dukart, Ambler, PA (US); Judy Lucas, Nanuet, NY (US); Lisa A. Speicher, Havertown, PA (US)

(73) Assignee: Wyeth, Madison, NJ (US)

( * ) Notice: Subject to any disclaimer, the term of this patent is extended or adjusted under 35 U.S.C. 154(b) by 982 days.

This patent is subject to a terminal disclaimer.

(21) Appl. No.: 09/659,643

(22) Filed: Sep. 12, 2000

Related U.S. Application Data

(60) Provisional application No. 60/240,944, filed on Sep. 15, 1999.

(51) Int. Cl.
| | |
|---|---|
| A01N 47/10 | (2006.01) |
| A01N 37/12 | (2006.01) |
| A01N 37/44 | (2006.01) |
| A01N 37/18 | (2006.01) |
| A01N 43/02 | (2006.01) |
| A61K 31/27 | (2006.01) |
| A61K 31/195 | (2006.01) |
| A61K 31/16 | (2006.01) |
| A61K 31/335 | (2006.01) |
| A61K 33/24 | (2006.01) |

(52) U.S. Cl. ............ 514/478; 514/566; 514/613; 514/449; 424/649

(58) Field of Classification Search .......... 514/19, 514/478–488; 424/649
See application file for complete search history.

(56) References Cited

U.S. PATENT DOCUMENTS

| | | | |
|---|---|---|---|
| 4,666,890 A | 5/1987 | Kitaura et al. | 514/18 |
| 5,312,831 A | 5/1994 | Ayral-Kaloustian et al. | 514/478 |
| 5,545,662 A * | 8/1996 | Ayral-Kaloustian et al. | 514/478 |

FOREIGN PATENT DOCUMENTS

| | | |
|---|---|---|
| WO | WO 99/42099 | 8/1999 |
| WO | WO 00 38665 | 7/2000 |

OTHER PUBLICATIONS

Windholz, M., Editor of The Merck Index, An Encyclopedia of Chemicals, Drugs, and Biologicals, 10th Edition, pp. 183, 329, 890-891, and 1427-1428, 1986.*
Stedman's Medical Dictionary, 25th Edition Illustrated, 1994, pp. 2871029, and 1030.*
Stein, J. H., Editor-in-Chief, Internal Medicine, Fourth Edition, 1994, Chapters 71 and 72.*
Goldman et al [Editors]. "Chapter 198: Principles of Cancer Therapy". Cecil's Textbook of Medicine (Twenty-First Edition, vol. 1). W.B. Saunders Company, 2000. pp. 1060-1074.*
Francis et al. "Paclitaxel (Taxol) and Docetaxel (Taxotere): Active Chemotherapeutic Agents in Lung Cancer". Lung Cancer, 1995; 12 Suppl 1:S163-S172.*
Klimp et al., Anticancer Res., 2000, 20(4), 2585-92.
Bezault et al., In Vivo, 1993, 7(6A), 487-91.
Daemen et al., J. Immunother., 1993, 13(1), 31-5.
D'Souza et al., Drug Dev. Ind. Pharm., 1999, 25(5), 583-90.
Grimm et al., Clin. Cancer Res., 2000, 6(10), 3895-903.
Verma et al., Cancer Biother. Radiopharm., 1996, 11(6), 349-54.
Mantovani et al., J. Immunother., 2000, 23(2), 267-74.
P.Kier: "high-dose chemotherapy and autologous stem-cell transplantation in breast cancer" Acta Medica Austriaca, vol. 27, No. suppl. 52, 2000, pp. 33-36 XP001009709 p. 33.

* cited by examiner

*Primary Examiner*—Ardin Marschel
*Assistant Examiner*—Leslie A Royds
(74) *Attorney, Agent, or Firm*—David A. Rubin; Anne M. Rosenblum

(57) ABSTRACT

This invention provides a method of treating solid tumors which comprises administering an effective amount of a combination of (1) a bioresponse modifier and (2) a chemotherapeutic agent. This invention also provides a method of potentiating the effects of a chemotherapeutic regimen in a mammal in need of treatment with such regimen which comprises administering a bioresponse modifier in addition to a chemotherapeutic regimen.

2 Claims, No Drawings

METHOD OF POTENTIATING CHEMOTHERAPY AND TREATING SOLID TUMORS

This application claims the benefit of U.S. Provisional Application No. 60/240,944, which was converted from U.S. patent application Ser. No. 09/396,051, filed Sep. 15, 1999, pursuant to a petition filed under 37 C.F.R. § 1.53 (c)(2)(i).

This invention relates to the use of a combination of a bioresponse modifier and a chemotherapeutic agent in the potentiation of chemotherapy and in the treatment of solid tumors.

Cancer chemotherapy for solid tumors has historically been focused on cytotoxic drugs that target essential metabolic processes (anti-metabolites) or general toxins (alkylating agents) that interfere with multiple metabolic processes. Antibiotic based drugs (doxorubicin, mitoxantrone, mitomycin C, etc.) target nucleic acid replication or integrity and are, therefore, generally toxic to cells. Similarly, microtubule active (taxanes, vinca alkaloids) compounds target structurally essential components of the cell, rendering these compounds generally toxic as well.

The trend in recent years toward combinations of drugs with somewhat different mechanisms of action has improved the response rate and survival for some solid tumors, including breast, prostate, and small cell lung cancer. Nevertheless, most solid tumors display a poor response rate with little demonstrable effect on survival. Included in this group of cancers are non-small cell lung, head and neck, stomach, pancreatic, cervical, melanoma, adrenal cortex, and soft tissue sarcomas. For these solid tumors in particular, and for solid tumors in general, new therapies are needed.

U.S. Pat. No. 5,312,831 discloses urethanes and ureas which induce cytokine production, that are useful in restoring neutrophils after cancer chemotherapy, radiation therapy, bone marrow transplantation, or infections, and are useful in the treatment of cancer, AIDS, aplastic anemia, myelodysplastic syndrome, infectious diseases, and the enhancement of the immune response.

U.S. Pat. No. 4,666,890 discloses a synthetic tripeptide which has been reported to have activity as an immunomodulator, for use as an antitumor agent rather than as an adjuvant to chemotherapy. The reported cell-wall components and their synthetic analogs are all peptides incorporating a D-glutamic acid (D-Glu) moiety q-linked to either lysine (Lys) or diaminopimelic acid (A2pm), with additional peptide bonds or fatty acyl groups flanking the two ends.

DESCRIPTION OF THE INVENTION

This invention provides a method of treating solid tumors which comprises administering an effective amount of a combination of (1) a bioresponse modifier and (2) a chemotherapeutic agent. This invention also provides a method of potentiating the effects of a chemotherapeutic regimen in a mammal in need of treatment with such regimen which comprises administering a bioresponse modifier in addition to a chemotherapeutic regimen. As used in this invention, the term a bioresponse modifier and a chemotherapeutic agent includes the administration of one or more agents of each category; thus, for example, the term a chemotherapeutic agent can include the administration of two chemotherapeutic agents.

Treating is defined as providing palliative treatment, or inhibiting the growth or eradicating the solid tumor for which treatment is administered.

For the purpose of defining the scope of this invention, a bioresponse modifier is an agent which activates the body's innate immune system, and typically includes cytokine inducers and immune adjuvants. Cytokine inducers are agents which induce the production of cytokines, and include cytokines such as IL-1, TNF; natural products such as muramyl dipeptide, lipopolysaccaride and beta-glucan; and synthetic cytokine inducers such as those disclosed in U.S. Pat. Nos. 5,312,831, and 4,666,890, the disclosures of which are hereby incorporated by reference. Cytokine inducers are the preferred bioresponse modifiers of this invention.

Particularly preferred cytokine inducers are those disclosed in U.S. Pat. No. 5,312,831 of Formula I, having the structure:

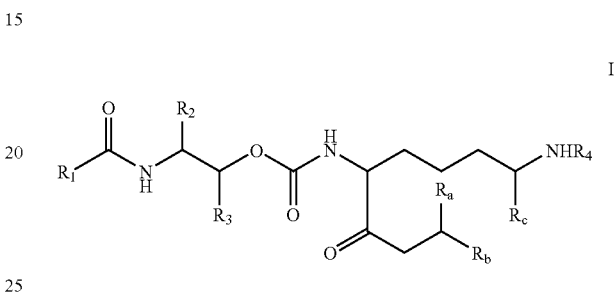

wherein $R_1$ is selected from the group consisting of hydrogen, a substituted or unsubstituted ($C_1$-$C_{20}$) alkyl group, a substituted or unsubstituted cycloalkyl group, a substituted or unsubstituted cycloalkylalkyl group, a vinyl group, an acetylene group, a substituted or unsubstituted amino group, a substituted or unsubstituted acylamino group, a substituted or unsubstituted aryl group, a substituted or unsubstituted aralkyl group, a substituted or unsubstituted aryloxy group, a substituted or unsubstituted alkoxyaryl group, a substituted or unsubstituted alkoxyaralkyl group and a substituted or unsubstituted monocyclic or bicyclic heterocyclic group containing from 1 to 4 hetero atoms selected from the group consisting of nitrogen, sulfur and oxygen atoms;

$R_a$ and $R_3$ are independently selected from hydrogen, substituted or unsubstituted ($C_1$-$C_6$) alkyl, substituted or unsubstituted alkoxyalkyl, substituted or unsubstituted cycloalkyl, substituted or unsubstituted cycloalkylalkyl, substituted or unsubstituted aryl, substituted or unsubstituted aralkyl, substituted or unsubstituted alkoxyaralkyl, vinyl, acetylene and a substituted or unsubstituted monocyclic or bicyclic heterocycle containing from 1 to 4 heteroatoms selected from the group consisting of nitrogen, sulfur and oxygen atoms provided that, in the case of $R_3$, the hetero atoms in said heterocycle are not directly bonded to the —CH— group of the —CH—X— moiety;

$R_2$, $R_b$ and $R_c$ are independently selected from carboxy or protected carboxy, carboxy or protected carboxyloweralkyl and carboxyamide;

X is oxygen or nitrogen;

$R_4$ is H or an amino protecting group; wherein the substituents in the aforementioned substituted alkyl, cycloalkyl, cycloalkylalkyl, amino, acylamino, aryl, aralkyl, aryloxy, alkoxyaryl, alkoxyaralkyl and heterocyclic groups are selected from the group consisting of halogen, hydroxyl, lower alkyl, lower alkoxy, aryloxy, aralkyloxy, amino, mono- or di-loweralkylamino, arylamino, aralkylamino, carboxyl, formyl, lower alkoxycarbonyl, aryloxycarbonyl, aralkyloxycarbonyl, loweralkylthio, arylthio, aralkylthio, arylsulfinyl, arylsulfinyl, aralkylsulfinyl, lower alkylsulfonyl, arylsulfonyl, aralkylsulfonyl and a monocyclic or bicyclic heterocyclic group having 1-4 hetero atoms selected from nitrogen, sulfur and oxygen;

or a pharmaceutically acceptable salt thereof.

The definitions of the substituents and methods of preparing the compounds of Formula I are provided in U.S. Pat. No. 5,312,831. The cytokine inducers of Formula I may contain one or more asymmetric carbons atoms; in such cases, the compounds of Formula I cover the individual diastereomers, the racemates, and the individual R and S entantiomers thereof.

It is particularly preferred that the cytokine inducer is [R-(R*,R*)]-N-[(R)-6-carboxy-$N^2$-[[2-carboxy-1-methyl-2-[(1-oxoheptyl)amino]ethoxy]carbonyl]-L-lysyl]-alanine or a pharmaceutically acceptable salt thereof (a compound of Formula I), which is disclosed as Example 28 of U.S. Pat. No. 5,312,831.

U.S. Pat. No. 5,312,831 discloses several standard pharmacologic test procedures which will enable one skilled in the art to evaluate whether compounds are bioresponse modifiers. For example, the test procedures in col. 16-17, evaluate the induction of IL-6, CSF, and G-CSF production.

It is preferred that the chemotherapeutic agent is a microtubular agent or a macrophage activating agent. Microtubular active compounds are defined as compounds that destabilize microtubules either by preventing polymerization of the protein tubulin (e.g., vincristine) or by preventing the depolymerization of tubulin (e.g., taxanes). The assembly and disassembly of microtubules is a dynamic process influenced by tubulin binding proteins and protein phosphorylation (kinases). Microtubular active compounds include taxanes, such as paclitaxcel or docetaxel, vincristine, vinblastine, vinorelbine, and the like. Macrophage activating agents are those compounds which activate macrophage activity, such as adriamycin, doxirubicin, and similar anthracenediones and anthracyclines, cisplatin, carboplatin, mitomycin C, bleomycin, and the like. It is preferred that the chemotherapeutic agent is paclitaxcel or carboplatin, or a combination of both. The microtubular agents or macrophage activating agents of this invention are either commercially available or can be prepared by standard procedures in the published literature.

The potentiating effect of bioresponse modifiers on chemotherapeutic agents was evaluated in an in vivo standard pharmacological test procedure in which a human non small cell type lung cancer (NSCLC) cell line was engrafted onto the flanks of immunodeficient nude mice. The following briefly describes the test procedure used and results obtained. [R-(R*,R*)]-N-[(R)-6-Carboxy-$N^2$-[[2-carboxy-1-methyl-2-[(1-oxoheptyl)amino]ethoxy]carbonyl]-L-lysyl]-alanine was used as a representative bioresponse modifier and paclitaxcel was used a representative chemotherapeutic agent.

Balb-c nu/nu female mice were obtained from Charles River Laboratories at 6-8 weeks of age and used experimentally at 8-10 weeks of age. The human non small-cell lung carcinoma (NSCLC) line H-157 was obtained from the American tissue culture collection (ATCC) (Bethesda, Md.). Cells were grown in RPMI medium with 10% fetal bovine serum.

Mice were injected subcutaneously with $7.5 \times 10^6$ H-157 NSCLC tumor cells. Tumors were allowed to develop until they reached a size of 80-150 mg. Tumor size was determined using vernier calipers to measure length (l) and width (w). The tumor volume was estimated using the formula $l \times w^2/2$. The volume in $mm^3$ can be converted to milligrams directly assuming unit density. Seven days after injection, mice were randomized (day 0) into groups of 10 with a mean tumor mass of 100 mg. Treatment groups received paclitaxcel (30 mg/kg) on day 0 and either vehicle or [R-(R*,R*)]-N-[(R)-6-Carboxy-$N^2$-[[2-carboxy-1-methyl-2-[(1-oxoheptyl)amino]ethoxy]carbonyl]-L-lysyl]-alanine (100 μg/kg) on days 1 and 8.

On days 7 and 14, tumor growth in groups receiving paclitaxcel plus [R-(R*,R*)]-N-[(R)-6-carboxy-$N^2$-[[2-carboxy-1-methyl-2-[(1-oxoheptyl)amino]ethoxy]carbonyl] L-lysyl]-alanine was significantly inhibited versus untreated controls or groups receiving paclitaxcel only. Paclitaxcel alone inhibited tumor cell growth measured on day 7 (p<0.05 by student's t test) and the degree of suppression was significantly enhanced by treatment with [R-(R*,R*)]-N-[(R)-6-carboxy-$N^2$-[[2-carboxy-1-methyl-2-[(1-oxoheptyl)amino]ethoxy]carbonyl]-L-lysyl]-alanine one day after paclitaxcel administration. By day 14, tumor growth in the paclitaxcel only group was not significantly suppressed versus control; however, the group receiving paclitaxcel on day 0 and [R-(R*,R*)]-N-[(R)-6-carboxy-N [[2-carboxy-1-methyl-2-[(1-oxoheptyl)amino]ethoxy]carbonyl]-L-lysyl]-alanine on days 1, 8 was still significantly suppressed when compared either to untreated controls or the paclitaxcel only group. The results obtained are shown below in Table 1. In the below table, [R-(R*,R*)]-N-[(R)-6-carboxy-$N^2$-[[2-carboxy-1-methyl-2-[(1-oxoheptyl)amino]ethoxy]carbonyl]-L-lysyl]-alanine is referred to as CI.

TABLE 1

The Effect of CI on Paclitaxcel Mediated Inhibiton of Tumor Cell Growth in Nude Mice Xenografts

| Treatment Group | [a]Tumor size (mg) Day 7 | % Suppression | Tumor size (mg) Day 14 | % Suppression |
|---|---|---|---|---|
| untreated control | 410 ± 99 | — | 1234 ± 354 | — |
| Paclitaxcel | [c]289 ± 108 | 30 | 866 ± 348 | 30 |
| Paclitaxcel + CI | [b]182 ± 69 | 56 | [b]491 ± 151 | 60 |

[a]data are from 5 independent evaluations (mean ± standard deviation) in which there were 10 mice/group in each evaluation. Treatment groups received paclitaxcel (30 mg/kg) on day 0 and either vehicle or CI (100 μg/kg) on day 1 and day 8.
[b]P ≤ 0.05 versus the untreated group or the paclitaxcel only group (Student's t test).
[c]P ≤ 0.05 versus the untreated control.

Several evaluations were performed in which tumor bearing mice received only [R-(R*,R*)]-N-[(R)-6-carboxy-$N^2$-[[2-carboxy-1-methyl-2-[(1-oxoheptyl)amino]ethoxy]carbonyl]-L-lysyl]-alanine (100 μg/kg) on days 1 and 8 after staging (data not shown). In none of these evaluations did [R-(R*,R*)]-N-[(R)-6-carboxy-$N^2$-[[2-carboxy-1-methyl-2-[(1-oxoheptyl)amino]ethoxy]carbonyl]-L-lysyl]-alanine by itself inhibit tumor cell growth in nude mice. [R-(R*,R*)]-N-[(R)-6-Carboxy-$N^2$-[[2-carboxy-1-methyl-2-[(1-oxoheptyl)amino]ethoxy]carbonyl]-L-lysyl]-alanine does not directly inhibit tumor cell growth in vitro nor does it potentiate the growth inhibitory effect of paclitaxcel in cell culture.

The effects of a bioresponse modifier and a chemotherapeutic agent were also evaluated in a clinical study. [R-(R*,R*)]-N-[(R)-6-Carboxy-$N^2$-[[2-carboxy-1-methyl-2-[(1-oxoheptyl)amino]ethoxy]carbonyl]-L-lysyl]-alanine was used as a representative bioresponse modifier, and paclitaxcel and carboplatin were used as representative chemotherapeutic agents. In this study, cancer patients with late stage disease were given a dose of [R-(R*,R*)]-N-[(R)-6-carboxy-$N^2$-[[2-carboxy-1-methyl-2-[(1-oxoheptyl)amino]ethoxy]carbonyl]-L-lysyl]-alanine (cycle 0) approximately 7 days before the first round of chemotherapy (carboplatin and paclitaxcel). Patients received a second round of chemotherapy approximately 21 days later and on days 1 and 8 after this 2nd chemotherapy treatment patients received [R-(R*,R*)]-N-[(R)-6-carboxy-N$^2$-[[2-carboxy-1-methyl-2-[(1-oxoheptyl)amino]ethoxy]carbonyl]-L-lysyl]-alanine at the doses indicated in table below. Sixty-nine percent of patients showed some clinical benefit either in the form of complete or partial reduction in tumor mass or stabilization of disease. Of the 16 patients treated, 6 had a presumed diagnosis of NSCLC. In this group, there were 3 complete responses, 1 partial response, one stabilization of disease and only 1 patient with progressive disease. Inasmuch as the expected complete response rate with the standard chemotherapy regimen (paclitaxcel and carboplatin) is approximately 5%, the finding that 3 of 6 treated patients showed a complete response was completely unexpected. In this treatment regimen, the dose of paclitaxcel was 175-200 mg/m$^2$ and the dose of carboplatin was the dose at which the area under the curve (AUC) equals 6 mg/ml×min. The results from the clinical trial are summarized in the table below. In the Table below, [R-(R*,R*)]-N-[(R)-6-carboxy-N$^2$-[[2-carboxy-1-methyl-2-[(1-oxoheptyl)amino]ethoxy]carbonyl]-L-lysyl]-alanine is referred to as CI.

TABLE 2

Treatment of Advanced Cancer Patients with a Combination of Paclitaxcel, Carboplatin and CI.

| #Patients treated | Dose (μg/kg)[b] | [a]Tumor Response | | | |
|---|---|---|---|---|---|
| | | Complete | Partial | Stable | Progressive |
| 3 | 0.1 | 2 | 1 | | |
| 6 | 0.2 | | 1 | 2 | 3 |
| 4 | 0.266 | 1 | 1 | 1 | 1 |
| 3 | 0.4 | 1 | | 1 | 1 |
| Total 16 | | 4 | 3 | 4 | 5 |

[a]Complete - no evidence of disease
Partial - >50% decrease in tumor mass
Stable - no further progression of disease
Progressive - disease progressed
[b]Dose of CI.

The results of the in vivo standard pharmacological test procedure and clinical trial using representative bioresponse modifiers and chemotherapeutic agents demonstrate that the combination of a bioresponse modifier with a chemotherapeutic agent is useful in potentiating standard chemotherapeutic regimens and is useful in treating solid tumors. In particular, the combination of this invention is useful in treating non-small cell lung carcinoma, glioma, cancers of the ovary, breast, prostate, head and neck, kidney, pancreas, liver, and colon, and soft tissue sarcoma.

As used in this invention, the combination regimen can be given simultaneously or can be given in a staggered regimen, with the bioresponse modifier being given at a different time during the course of chemotherapy. Therefore, the term combination does not necessarily mean administered at the same time or as a unitary dose. For example, the regimen in the clinical study typifies a therapeutically useful regimen, in which patients received a bioresponse modifier before receiving the first course of chemotherapy. As typical for chemotherapeutic regimens, the course of chemotherapy is repeated several weeks later, and in this case, the bioresponse modifier was administered one or more days after the administration of the second course of chemotherapy. This course of staggered administration can be continued throughout the treatment period.

The components of the combination can be formulated into a unitary dosage form, for simultaneous administration, however, it is anticipated that the components of the combinations will be formulated for separate administration.

Formulations for specific chemotherapeutic agents are well known in the art (and most used will typically be commercially available or already formulated for use in clinical trials), with such agents typically administered intravenously or orally; however, as each agent and patient varies, the chemotherapeutic agents may also be administered by parenteral injection, rectally, vaginally, transdermally, subcutaneously, topically, intranasally, or by direct infusion to the site of the lesion.

The bioresponse modifiers of this invention may also be administered orally, intravenously, parenterally, rectally, vaginally, transdermally, subcutaneously, topically, intranasally, or by direct infusion to the site of the lesion. The bioresponse modifiers can be formulated according to standard literature methodology. For example, formulations for the compounds of Formula I and [R-(R*,R*)]-N-[(R)-6-carboxy-N$^2$-[[2-carboxy-1-methyl-2-[(1-oxoheptyl)amino]ethoxy]carbonyl]-L-lysyl]-alanine are provided in U.S. Pat. No. 5,312,831.

Bioresponse modifiers and chemotherapeutic agents which are not commercially available or available in clinical trials (or in which it is undesirable to use such existing formulations) may be formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

Formulation for tablet or capsule administration may include solid carriers including starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

These components of the combination may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

It is anticipated that the dosage of chemotherapeutic agents and bioresponsive modifiers will be adjusted during the course of treatment, according to patient response to treatment and toxicity inherent in standard chemotherapeutic regimens. For example, the dosage of chemotherapeutic agents is typically lowered upon observation of myelosuppression or impaired hepatic function. As a starting dosage, it is anticipated that the initial dosages of chemotherapeutic agents will be the dosages which would be used absent combination with a bioresponse modifier. For example, for a regimen consisting of paclitaxcel, carboplatin and [R-(R*,R*)]-N-[(R)-6-carboxy-$N^2$-[[2-carboxy-1-methyl-2-[(1-oxoheptyl)amino]ethoxy]carbonyl]-L-lysyl]-alanine, it is anticipated that the dosage of paclitaxcel would be 135-225 mg/m$^2$, with 175-200 mg/m$^2$ being preferred, and the dose of carboplatin would be the dose at which the area under the curve (AUC) equals 5-7 mg/ml×min, with 6 mg/ml×min being preferred. Projected dosages of the bioresponse modifiers will vary according to their potency in inducing the immune system; for cytokine inducers, their potency in inducing the production of cytokines. For [R-(R*,R*)]-N-[(R)-6-carboxy-$N^2$-[[2-carboxy-1-methyl-2-[(1-oxoheptyl)amino]ethoxy]carbonyl]-L-lysyl]-alanine it is anticipated that the initial dosage will range from 0.005-2 µg/kg, with 0.01-1 µg/kg being preferred.

The invention claimed is:

1. A method of treating a non-small cell lung tumor in a mammal which comprises administering to said mammal an effective amount of a combination comprising a cytokine inducer and a chemotherapeutic agent, wherein the cytokine inducer is [R-(R*,R*)]-N-[(R)-6-carboxy-$N^2$-[[2-carboxy-1-methyl-2-[(1-oxoheptyl)amino]-ethoxy]carbonyl]-L-lysyl]-alanine or a pharmaceutically acceptable salt thereof, and the chemotherapeutic agent is paclitaxel or a combination of paclitaxel and carboplatin, and wherein said combination of the cytokine inducer and the chemotherapeutic agent has a greater tumor suppressing effect than that of the chemotherapeutic agent alone.

2. The method according to claim 1, wherein the chemotherapeutic agent is the combination of paclitaxel and carboplatin.

* * * * *